United States Patent
Lew et al.

(10) Patent No.: US 11,524,036 B2
(45) Date of Patent: Dec. 13, 2022

(54) METHOD FOR TREATING THYROID ASSOCIATED OPHTHALMOPATHY

(71) Applicant: SUNGKWANG MEDICAL FOUNDATION, Seoul (KR)

(72) Inventors: He Len Lew, Seoul (KR); Mi Ra Park, Seoul (KR); Gi Jin Kim, Seongnam-si (KR)

(73) Assignee: SUNGKWANG MEDICAL FOUNDATION, Seoul (KR)

( * ) Notice: Subject to any disclaimer, the term of this patent is extended or adjusted under 35 U.S.C. 154(b) by 386 days.

(21) Appl. No.: 16/639,319

(22) PCT Filed: Aug. 16, 2018

(86) PCT No.: PCT/KR2018/009417
§ 371 (c)(1),
(2) Date: Feb. 14, 2020

(87) PCT Pub. No.: WO2019/035668
PCT Pub. Date: Feb. 21, 2019

(65) Prior Publication Data
US 2020/0246392 A1    Aug. 6, 2020

(30) Foreign Application Priority Data
Aug. 16, 2017   (KR) .................. 10-2017-0103723

(51) Int. Cl.
| | |
|---|---|
| A61K 35/50 | (2015.01) |
| A23L 33/10 | (2016.01) |
| A61K 9/00 | (2006.01) |
| C12N 5/0775 | (2010.01) |

(52) U.S. Cl.
CPC .............. *A61K 35/50* (2013.01); *A23L 33/10* (2016.08); *A61K 9/0051* (2013.01); *C12N 5/0668* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2013/0209422 A1 | 8/2013 | Kang et al. | |
| 2017/0065639 A1* | 3/2017 | Hantash | C12N 5/0663 |

FOREIGN PATENT DOCUMENTS

| | | | |
|---|---|---|---|
| CN | 106479969 A | | 3/2017 |
| WO | WO 2016/117960 | * | 7/2016 |

OTHER PUBLICATIONS

Lee, J. et al. Association Between MTHFR Polymorphisms and Susceptibility to Graves' Ophthalmopathy. Molecular Medicine Reports 14(3)2276-2282, Sep. 2016. (Year: 2016).*

International Search Report dated Mar. 28, 2019 in PCT/KR2018/009417, 4 pages.
Katarzyna Kozdon, et al. "Mesenchymal Stem Cell-Like Properties of Orbital Fibroblasts in Graves' Orbitopathy" Investigative Ophthalmology & Visual Science, vol. 56, No. 10, Sep. 2015, pp. 5743-5750.
Reine El Omar, et al., Umbilical Cord Mesenchymal Stem Cells: The New Gold Standard for Mesenchymal Stem Cell-Based Therapies? Tissue Engineering, vol. 20, No. 5, 2014, pp. 523-544.
Cheng Zhao, et al. "Umbilical Cord-Derived Mesenchymal Stem Cells Inhibit Cadherin-11 Expression by Fibroblast-Like Synoviocytes in Rheumatoid Arthritis" Journal of Immunology Research, vol. 2015, Article ID: 137695, 2015, 10 pages.
Marta Elena Castro Manrreza, "Participation of Mesenchymal Stem Cells in the Regulation of Immune Response and Cancer Development" Boletin Medico del Hospital Infantil de Mexico, vol. 73, No. 6, 2016, pp. 380-387.
Jung Min Lee, et al. "Comparison of Immunomodulatory Effects of Placenta Mesenchymal Stem Cells with Bone Marrow and Adipose Mesenchymal Stem Cells" International Immunopharmacology, vol. 13, 2012, pp. 219-224.
Robin L. Van, et al. "Cytological and Enzymological Characterization of Adult Human Adipocyte Precursors in Culture" The Journal of Clinical Investigation, vol. 58, Sep. 1976, pp. 699-704 and cover page.
Mark F. Pittenger, et al., "Multilineage Potential of Adult Human Mesenchymal Stem Cells" Science, vol. 284, Apr. 2, 1999, pp. 143-147 and cover pages.
Office Action dated Mar. 9, 2021 in corresponding Japanese Patent Application No. 2020-508318 (with English Translation), 10 pages.
Extended European Search Report dated Apr. 19, 2021 in corresponding European Patent Application No. 18845495.3, 8 pages.
Hyun-Jung Lee et al., "In Vitro Screening System for Hepatotoxicity: Comparison of Bone-Marrow-Derived Mesenchymal Stem Cells and Placenta-Derived Stem Cells", Journal of Cellular Biochemistry, 2011, vol. 112, pp. 49-58.
Haizhi Qi et al: "Foxp3-modified Bone Marrow Mesenchymal Stem Cells Promotes Liver Allograft Tolerance Through the Generation of Regulatory T Cells in Rats", Journal of Translational Medicine, Biomed Central, vol. 13, No. 1, XP021228520, Aug. 21, 2015, pp. 1-13.
Aaron W Joe et al: "Mesenchymal Stem Cells and Potential Applications in Treating Ocular Disease", Current Eye Research, vol. 35, No. 11, Oct. 19, 2010, pp. 941-952.

* cited by examiner

*Primary Examiner* — Ralph J Gitomer
(74) *Attorney, Agent, or Firm* — Oblon, McClelland, Maier & Neustadt, L.L.P.

(57) ABSTRACT

Provided is a composition including mesenchymal stem cells as an effective ingredient for prevention, alleviation, or treatment of thyroid-associated ophthalmopathy. A pharmaceutical composition including mesenchymal stem cells as an effective ingredient for treatment of thyroid-associated ophthalmopathy allows patients with thyroid-associated ophthalmopathy to recover from an abnormal increase in hyaluronic acid production in orbital fibroblasts, increased adipocyte differentiation, and increased lipid accumulation, and thus may be useful for the treatment of thyroid-associated ophthalmopathy.

7 Claims, 8 Drawing Sheets

Specification includes a Sequence Listing.

METHOD FOR TREATING THYROID ASSOCIATED OPHTHALMOPATHY

TECHNICAL FIELD

The present disclosure relates to a composition for prevention, alleviation, or treatment of thyroid-associated ophthalmopathy.

BACKGROUND ART

Thyroid-associated ophthalmopathy (TAO) is a chronic orbital inflammatory disease associated with thyroid disorders and is observed in about 60% of patients with thyroid dysfunction. An increase in differentiation of orbital fibroblasts to lipocytes and an increase in hyaluronic acid are generally observed in patients with TAO, resulting in hypertrophy or inflammation of the lipocytes around the eye. When patients miss the right time for treatment, serious sequelae such as eyelid retraction, proptosis, restricted strabismus, decreased vision, diplopia, or decreased vision, and thus patients should receive appropriate treatment. Until now, high concentrations of steroids, radiotherapy, and orbital decompression techniques have been used for the treatment of TAO, but the effects are limited, and there are side effects and risks related to the treatment.

Therefore, there is an urgent need to develop a novel therapeutic agent for treating thyroid ophthalmopathy, which is an intractable orbital inflammatory disease.

DESCRIPTION OF EMBODIMENTS

Technical Problem

Provided is a composition including mesenchymal stem cells as an effective ingredient for prevention, alleviation, or treatment of thyroid-associated ophthalmopathy.

Solution to Problem

According to an aspect of the present disclosure, provided is a mesenchymal stem cell that expresses at least one selected from the group consisting of forkhead box P3 (FOXP3), human leukocyte antigen G (HLA-G), and toll-like receptor 4 (TLR4).

The mesenchymal stem cell may have characteristics a) or b) below:

a) a characteristic that expresses at least one selected from the group consisting of chemokine (C-X-C motif) ligand 1 (CXCL-1), monocyte chemotactic protein 1 (MCP-1), and tissue inhibitors of metalloproteinases (TIMP-1);

b) a surface antigen character of at least one selected from the group consisting of CD90, CD146, CD105, and CD72.

As used herein, the term "mesenchymal stem cells (MSCs)" may refer to cells capable of maintaining self-renewal and sternness maintenance and differentiating into various mesenchymal tissues, and the cells may include mesenchymal stem cells of mammals, such as animals including humans. Also, the mesenchymal stem cells may be umbilical cord-derived, umbilical cord blood-derived, bone marrow-derived, placenta-derived, or adipose-derived mesenchymal stem cells. The placenta-derived mesenchymal stem cells may be derived from various tissues consisting the placenta, and examples of the tissues may include amnion epithelial cells, amniotic membranes, trophoblasts, and chorionic membranes. Preferably, the placenta-derived mesenchymal stem cells may be derived from a chorionic plate of the placenta and, more preferably, may be derived from a chorionic plate membrane. Isolation of mesenchymal stem cells can be performed by using methods known to those skilled in the art, and examples of the methods are disclosed in reference documents such as Pittenger et al. (Science 284: 143, 1997) and van et al. (J. Clin. Invest., 58: 699, 1976).

The mesenchymal stem cells may express or secrete immune cytokines. The mesenchymal stem cell may express or secrete more immune cytokines than control groups, fibroblasts, or other cells do. Examples of the immune cytokines may include CXCL-1, MCP-1, or TIMP-1.

Also, the mesenchymal stem cells may express or secrete FOXP3, HLA-G, or TLR4. The mesenchymal stem cell may express or secrete more FOXP3, HLA-G, or TLR4 than control groups, fibroblasts, or other cells do. The mesenchymal stem cells may express or secrete more FOXP3, HLA-G, or TLR4 than bone marrow-derived or adipose-derived mesenchymal stem cells do. The difference in expression levels may be, for example, the result of comparing the expressions of genes and proteins at an mRNA or protein level. Also, the difference in expression levels may be, for example, by microarray and proteomics analysis.

In addition, the mesenchymal stem cells may be genetically engineered to increase expression of any one or more of the factors. As used herein, the term "genetic engineering" or "genetically engineered" refers to an act of introducing one or more genetic modifications to a cell; or the cell thus prepared. For example, the mesenchymal stem cells or host cells are genetically engineered to increase the expression or activity of CXCL-1, MCP-1, or TIMP-1, or, for example, may include an exogenous gene encoding CXCL-1, MCP-1, TIMP-1, or an active fragment thereof. The activity increase may denote that the activity of the same type of protein or enzyme is higher compared to the activity of an endogenous protein or enzyme that does or does not have a given genetically unengineered parent cell (e.g., wild type). The exogenous gene may be expressed in an amount sufficient to increase the activity of the protein in the mesenchymal stem cell or host cell compared to that of the parent cell. The exogenous gene may be introduced into the parent cell through an expression vector. Also, the exogenous gene may be introduced into the parent cell in the form of a linear polynucleotide. In addition, the exogenous gene may be expressed from an expression vector (e.g., plasmid) in a cell. Also, the exogenous gene may be inserted into and expressed in the genetic material (e.g., chromosome) in the cell for stable expression.

In addition, the mesenchymal stem cell may express CD90, CD146, CD105, or CD72. Particularly, the mesenchymal stem cells provided herein may express at least about 20%, 25%, 30%, 35%, 40%, 45%, 50%, 55%, 60%, 65%, 70%, 75%, 80%, 85%, 90%, 95%, 98%, or about 99% of CD90, CD146, CD105, or CD72 positive surface markers with respect to cell markers expressed on the cell surface. In addition, the mesenchymal stem cells provided herein may express about at least about 70% or less, at least about 60% or less, at least about 50% or less, at least about 40% or less, at least about 30% or less, at least about 20% or less, at least about 10% or less, at least about 5% or less, or at least about 1% or less of CD45, CD31, CD34, or HLA-DR negative markers with respect to cell markers expressed on the cell surface. As used herein, the term "positive" may denote that markers regarding stem cell marking are present in a greater amount or at a higher concentration compared to those of non-stem cells to which the marking is referred. That is, a cell have a marker existing in or on surface of the cell, and thus when the cell may be distinguished from at least one other cell type by using the marker, the cell is positive with respect to the marker. Also, the positive cell may denote that the cell has the marker in an amount sufficient to signal, for example, a signal of a cytometry device, at a value greater than the background value. For example, a cell may be labeled as detectable with a CD90-specific antibody, and when the signal from the antibody is detectably greater than the control group (e.g. the background value), the cell is "CD90+". As used herein, the term "negative" denotes that a marker compared to the background value may not be detected even when an antibody specific to a particular cell surface marker is used. For example, when a cell may not be labeled as detectable with a CD45-specific antibody, the cell is "CD45-".

According to another aspect of the present disclosure, provided is a pharmaceutical composition including mesenchymal stem cells as an effective ingredient for treatment of thyroid-associated ophthalmopathy.

According to another aspect of the present disclosure, provided is a use of the mesenchymal stem cells for preparation of cell therapy products and pharmaceutical compositions or formulas.

According to another aspect of the present disclosure, provided is a use of the mesenchymal stem cell or a cell population, a culture, a lysate, or an extract thereof for preparation of medicine for treatment or prevention of thyroid-associated ophthalmopathy.

According to another aspect of the present disclosure, provided is a method of treating or preventing thyroid-associated ophthalmopathy, the method including administering the mesenchymal stem cell or a cell population, a culture, a lysate, or an extract thereof as an effective ingredient to a subject in need of the effective ingredient.

As used herein, the term "treatment" refers to or includes alleviation, suppression of progress, or prevention of a disease, disorder, or condition or at least one symptom thereof. As used herein, the term "effective ingredient" or "pharmaceutically effective dose" may refer to an arbitrary amount of the composition that is used in the process of performing the disclosure provided in the present specification sufficient for alleviation, suppression of progress, or prevention of a disease, disorder, or condition or at least one symptom thereof.

As used herein, the term "thyroid-associated ophthalmopathy (TAO)" refers to an orbital inflammatory disease that occurs in association with hyperthyroidism caused by excessive secretion of thyroid hormones. The symptoms may include eyelid retraction, proptosis, restricted strabismus, decreased vision, diplopia, or decreased vision.

As an alternative of the mesenchymal stem cells, a culture, lysate, or extract thereof may be used. The culture, lysate, or extract may be a useful alternative when the cell itself cannot be used, and since the culture, lysate, or extract includes components of cells such as protein, the alternative may exhibit biological activities similar to or same as those of the original cells. The lysate or extract may be obtained by using a commercially available cell lysis kit or extraction kit.

The pharmaceutical composition may be for ocular administration. As used herein, the terms "administering", "introducing", and "transplanting" may be interchangeably used and may refer to an arrangement of the composition according to an embodiment into the subject by using a method or a pathway resulting at least partial localization of the composition according to an embodiment to the desired site. The administration may be performed via an arbitrary appropriate pathway which delivers a cell or at least a part of cell components of the composition according to an embodiment to the desired site in an alive subject. The survival time of the cell after administered into the subject may be as short as several hours, for example, 24 hours to several days, or as long as several years.

The composition according to an embodiment may include about 0.001 weight percent (wt %) to about 80 wt % of the mesenchymal stem cells with respect to the total weight of the composition. Also, a dose of the composition may be in a range of 0.01 mg to 10,000 mg, 0.1 mg to 1000 mg, 1 mg to 100 mg, 0.01 mg to 1000 mg, 0.01 mg to 100 mg, 0.01 mg to 10 mg, or 0.01 mg to 1 mg. Also, a dose of the mesenchymal stem cells may be in a range of $1.0 \times 10^5$ to $1.0 \times 10^8$ cells/kg (body weight). However, the dose may be variously prescribed by factors such as the formulation method, mode of administration, age, weight, sex, morbidity, food, time of administration, route of administration, rate of excretion, and reaction sensitivity of the patient, and those skilled in the art may appropriately control the dose in consideration of these factors. A number of administration may be one, but may be two or more within the range of clinically acceptable side effects, and, regarding an administration site, the administration may be performed at one site or at least two sites. In case of animals other than humans, the same dose per kg used for humans or the dose converted by a volume ratio (e.g., an average value) of an organ (e.g., heart) between the target animal and a human may be administered. Possible routes of administration may include oral, sublingual, parental (e.g., subcutaneous, intramuscular, intraarterial, intraperitoneal, intradural, or intravenous), rectal, topical (including transdermal), inhalation, and injection, eye drop or implantation device, or material insertion. The target animals to be treated according to an embodiment may include humans and mammals for other purposes, and examples of the animals may include humans, monkeys, mice, rats, rabbits, sheep, cattle, dogs, horses, and pigs.

The pharmaceutical composition according to an embodiment may include a pharmaceutically acceptable carrier and/or additive. For example, the pharmaceutical composition may include sterile water, saline, conventional buffers (phosphoric acid, citric acid, other organic acids, etc.), stabilizers, salts, anti-oxidants (ascorbic acid, etc.), surfactants, suspensions, isotonic agents, or preservatives. For topical administration, it may be desirable to combine the pharmaceutical composition with organic materials such as biopolymers, inorganic materials such as hydroxyapatite, particularly collagen matrix, polylactic acid polymers or copolymers, polyethylene glycol polymers or copolymers, and chemical derivatives thereof. When the pharmaceutical composition according to an embodiment is prepared in a formulation suitable for injection, the mesenchymal stem cells may be dissolved in a pharmaceutically acceptable carrier or frozen in a dissolved solution.

The pharmaceutical composition according to an embodiment may appropriately include suspensions, dissolution aids, stabilizers, isotonic agents, preservatives, anti-adhesion agents, surfactants, diluents, excipients, pH adjusting agents, pain relieving agents, buffers, reducing agents, and anti-oxidants if necessary according to the administration method or preparation. Pharmaceutically acceptable carriers and preparations suitable for the present invention including those mentioned above are described in detail in Remington's Pharmaceutical Sciences, 19th ed., 1995. The pharmaceutical composition according to an embodiment can be formulated by using pharmaceutically acceptable carriers and/or excipients according to methods which may be easily carried out by those skilled in the art so that the composition may be manufactured as a unit dosage form or incorporated into a multiple dose container. Here, the dosage forms may be a solution, suspension, or emulsion in oil or aqueous medium, or powders, granules, tablets, or capsules.

According to another aspect of the present disclosure, provided is a composition for health functional food including mesenchymal stem cells or a culture, lysate, or extract thereof for prevention or alleviation of thyroid-associated ophthalmopathy.

The composition for health functional food may include other food or food component in addition to the mesenchymal stem cells and may be appropriately used according to common methods. A mixing amount of the effective ingredient may be appropriately determined according to the purpose of use (prevention, health, or therapeutic treatment). In general, during preparation of the health functional food, the composition of the present disclosure may be added at an amount of 15 parts by weight or less with respect to the raw material. A type of the health food is not particularly limited.

The present inventors have found that mesenchymal stem cells reduce abnormal activity (excessive hyaluronic acid production, adipogenesis, and lipid accumulation) of fibroblasts in patients with thyroid-associated ophthalmopathy, and thus a composition including the mesenchymal stem cells may be useful as a composition for treatment, prevention, or alleviation of thyroid-associated ophthalmopathy.

Advantageous Effects of Disclosure

According to one or more embodiments, a pharmaceutical composition including mesenchymal stem cells as an effective ingredient for treating thyroid-associated ophthalmopathy reduces abnormal activity of orbital fibroblasts, and thus the pharmaceutical composition may be useful in treating thyroid-associated ophthalmopathy.

MODE OF DISCLOSURE

Figure 1A:
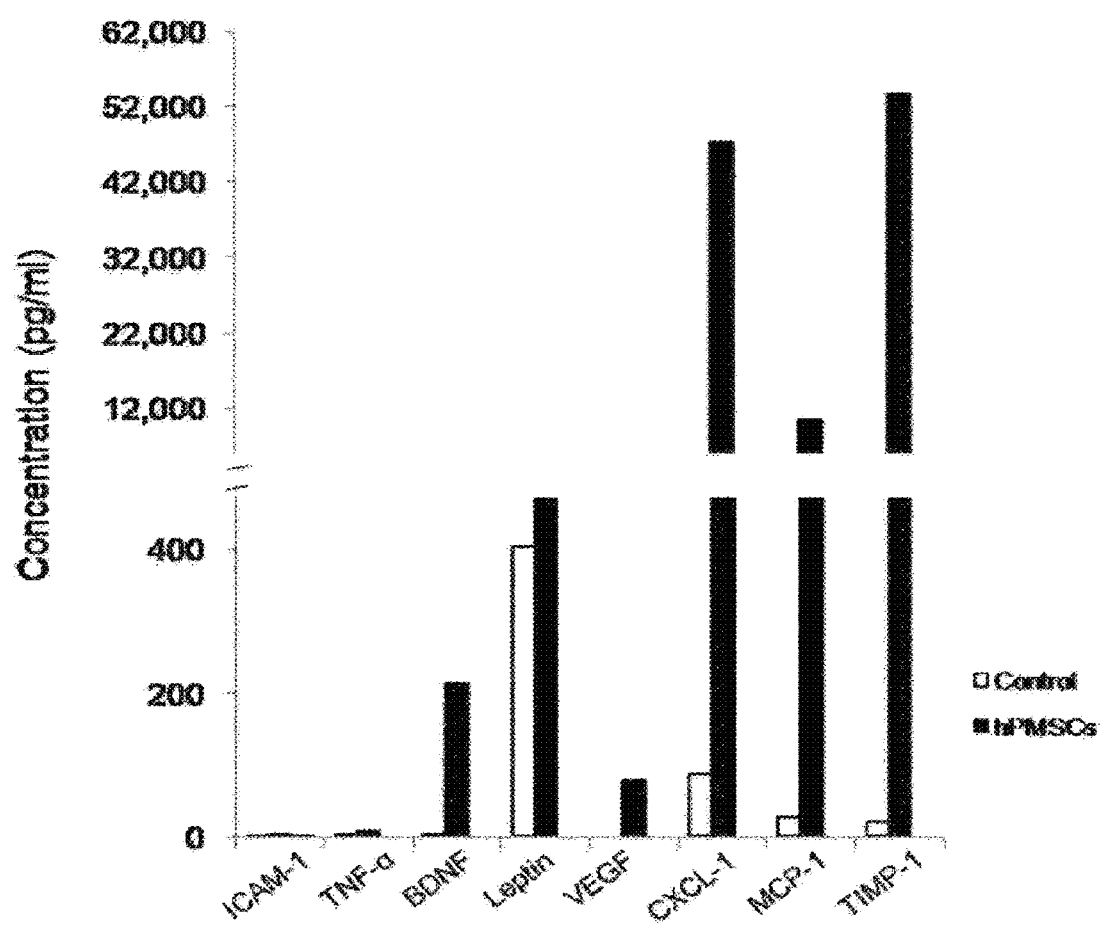
FIG. 1A shows levels of neuro-protective cytokines of human placenta-derived mesenchymal stem cells (hPMSCs) measured from a cell culture medium.

Hereinafter, the present invention will be described in more detail with reference to Examples. However, these examples are for illustrative purposes only and the scope of the present invention is not limited to these examples.

Reference Example

Reference Example 1

Isolation of Placenta-Derived Mesenchymal Stem Cells

An informed consent based on sufficient explanation beforehand was received from a healthy mother who normally delivered a baby, and an umbilical cord was separated from placenta tissues collected at the time of normal placenta delivery. The separated tissues (chorioamniotic membranes) were added to a 50-ml tube, DPBS was added to remove excess blood, and in 20 ml of enzyme solution I (1 mg/ml collagenase type I, 2 mg/ml Trypsin, 20 mg/ml DNase I, 1.2 U/ml Dispase, ×1 PS in HBSS) the suspension solids collected by scraping the upper part of the chorioamniotic membranes with sterilized slide glass were gathered on one side. 10 ml of the enzyme solution I was added, homogenously mixed, and a 37° C. enzyme reaction was repeated twice for 15 minutes to isolate stem cells from the tissues. The isolated cell suspension was centrifuged, and the isolated cells were cultured by using DMEM/F12 to which 10% fetal bovine serum, 1% penicillin-streptomycin, 1 ug/ml heparin, and 25 ng/ml fibroblast growth factor-4 (FGF-4) were added. The culture medium was replaced at an interval of 4 to 5 days, and TrypLE available from Invitrogen was passage-cultured for a short period of time (3 minutes) in a 37° C. incubator at the first passage.

Reference Example 2

Orbital Fibroblast Culture and Treatment

Orbital fibroblasts from humans (4 normal people, 4 patients) were obtained and cultured in DMEMFI2 (available from Gibco) (including 10% FBS and 1% penicillin-streptomycin). Two days after distributed and grown in a medium, the fibroblasts were mixed with 5 g/ml insulin, 1 mM dexamethasone, and 0.5 mM IBMX in DMEM (10% FBS), and thus differentiation into adipocytes was started (day 0). After 72 hours (day 3), the medium was replaced with a DMEM medium supplemented with 10% FBS and 5 μg/ml insulin, followed by supplying a DMEM medium supplemented with 10% FBS every other day.

Reference Example 3

Orbital Fibroblast Lipid Accumulation Analysis

Orbital fibroblasts from normal people and patients were placed in differentiation medium inducing adipose production, and then the cells were cultured for 10 days as in co-culturing with human placenta-derived mesenchymal stem cells (hPMSCs) and not co-culturing (for the first 4 days with DMEM supplemented with 10% FBS, 33 uM biotin, 17 uM pantothenic acid, 0.2 nM T3, 10 µg/mL transferrin, 0.2 uM prostaglandin I2, 0.1 mM isobutylmethylxanthine (IBMX), 1 uM dexamethasone, and 5 ug/ml insulin; and the next 5 to 10 days, without IBMX, dexamethaxone, and insulin). After 10 days, change in lipid accumulation of the fibroblasts was observed by Oil-Red-O staining.

Reference Example 4

Tear Sampling

Tears were collected from normal people (n=13) and thyroid-associated ophthalmopathy (TAO) patients (n=13) by using schirmer strips. Then, the schirmer strips were moved to a 0.5 ml-tube having cannula on the bottom, and 30 µL of PBS was added thereto. The content of the tube was moved to a larger tube (1.5 ml), and centrifuged for 5 minutes (13,000 rpm). The tears thus collected were preserved at −20° C.

Reference Example 5

Real-Time PCR

In day 8 of the culturing, hPMSCs ($2\times10^5$) were co-cultured with orbital fibroblasts for 48 hours. The cell lysate was homogenized in TRIzol (available from Invitrogen, Carlsbad, Calif., USA) to extract RNA. 1 µg of the total RNA from the samples was reverse transcript to synthesize cDNA. Conditions for synthesizing cDNA are as follows: RNA fusion (65° C., 1 minute), annealing (25° C., 5 minutes), amplification (42° C., 60 minutes), and enzyme inactivation (85° C., 1 minute).

Normalization was performed by amplifying mRNA of each gene according to the following PCR conditions: initial fusion (95° C., 2 minutes), amplification (95° C., 10 seconds; 55° C., 20 seconds; and 72° C., 20 seconds) 40 cycles. PPARγ, ADIPONECTIN, and C/EBPα, primer sets are as follows:

PPARγ FP: 5'-TTGACCCAGAAAGCGATTCC(SEQ ID NO: 1)-3', RP: 5'-AAAGTTGGTGGGCCAGAATG(SEQ ID NO: 2)-3'; ADIPONECTIN FP: 5'-GGCCGTGATGATGGCAGAGAT(SEQ ID NO: 3)-3', RP: 5'-TTTCACCGATGTCTCCCTTAGG(SEQ ID NO: 4)-3' C/EBPα FP: 5'-TGTATACCCCTGGTGGGAGA(SEQ ID NO: 5)-3', RP: 5'-TCATAACTCCGGTCCCTCTG(SEQ ID NO: 6)-3'. The mRNA expression of each of the genes was normalized to 18s rRNA. Data are depicted as folds (mean±SEM) of a factor related to adipose differentiation compared to the normal group.

Reference Example 6

Western Blot

Lysates were prepared by using a RIPA buffer. The total protein of the same amount was separated by SDS-PAGE and transferred to a membrane. The membrane was immunoblotted with anti-HAS1 and HAS2 (available from SantaCruz Biotechnology, SA, USA) at 1:1000 dilution, and the same membrane was cultured with GAPDH (available from SantaCruz). After washing, the resultant was cultured with horseradish peroxidase-conjugated anti-goat IgG secondary antibody at 1:10000 dilution at room temperature for 3 hours. The immune response bands were made into images by using an enhanced chemiluminescence solution (available from Animal Genetics, Suwon, Korea) and detected with the ChemiDoc™ XRS+ System Imager (available from Bio-Rad Laboratories, Hercules, Calif., USA). Protein expression levels were normalized to GAPDH. Data are depicted as folds (mean±SEM) of HAS2 compared to the normal group.

Reference Example 7

Enzyme-Linked Immunosorbent Assay (ELISA)

Tears taken from the normal people and TAO patients were prepared, and levels of hyaluronic acid (Ha) and hyaluronidase (Hyal) of the tears were determined by the ELISA. The present analysis was performed according to manual of the manufacturer.

Reference Example 8

FACS Analysis

Human fibroblasts ($3\times10^5$) were dissociated with a cell dissociation buffer (Life Technologies) and washed with PBS (2% (v/v) FBS). The resultant was cultured with an isotype control IgG or an antigen-specific antibody (BD Biosciences, CA, USA) for 20 minutes was used to identify cells. FACS sorting was performed by using a FACS vantage Flow Cytometer (BD Biosciences, CA, USA)

Example 1

Characteristic Analysis of Placenta-Derived Stem Cells

In order to analyze characteristics of the placenta-derived mesenchymal stem cells isolated in the same manner as in Reference Example 1, cytokine secretion characteristics and surface antigen characteristics of the cells were analyzed. In particular, concentrations of neuro-protective cytokines of the placenta-derived mesenchymal stem cells in the culture medium were measured by the ELISA, characteristics of surface antigens (CD34, CD45, CD90, CD31, HLA-DR, CD146, CD106, and CD73) of the placenta-derived mesenchymal stem cells were analyzed by FACS analysis, and the results are shown in FIG. 1.

FIG. 1A shows levels of neuro-protective cytokines of human placenta-derived mesenchymal stem cells (hPMSCs) measured from a cell culture medium. As shown in FIG. 1A, it was confirmed that secretion of cytokines related to inflammatory response and would healing (CXCL-1, MCP-1, and TIMP-1) in the culture solution of culturing hPMSCs was increased as the result of the ELISA.

Figure 1B:
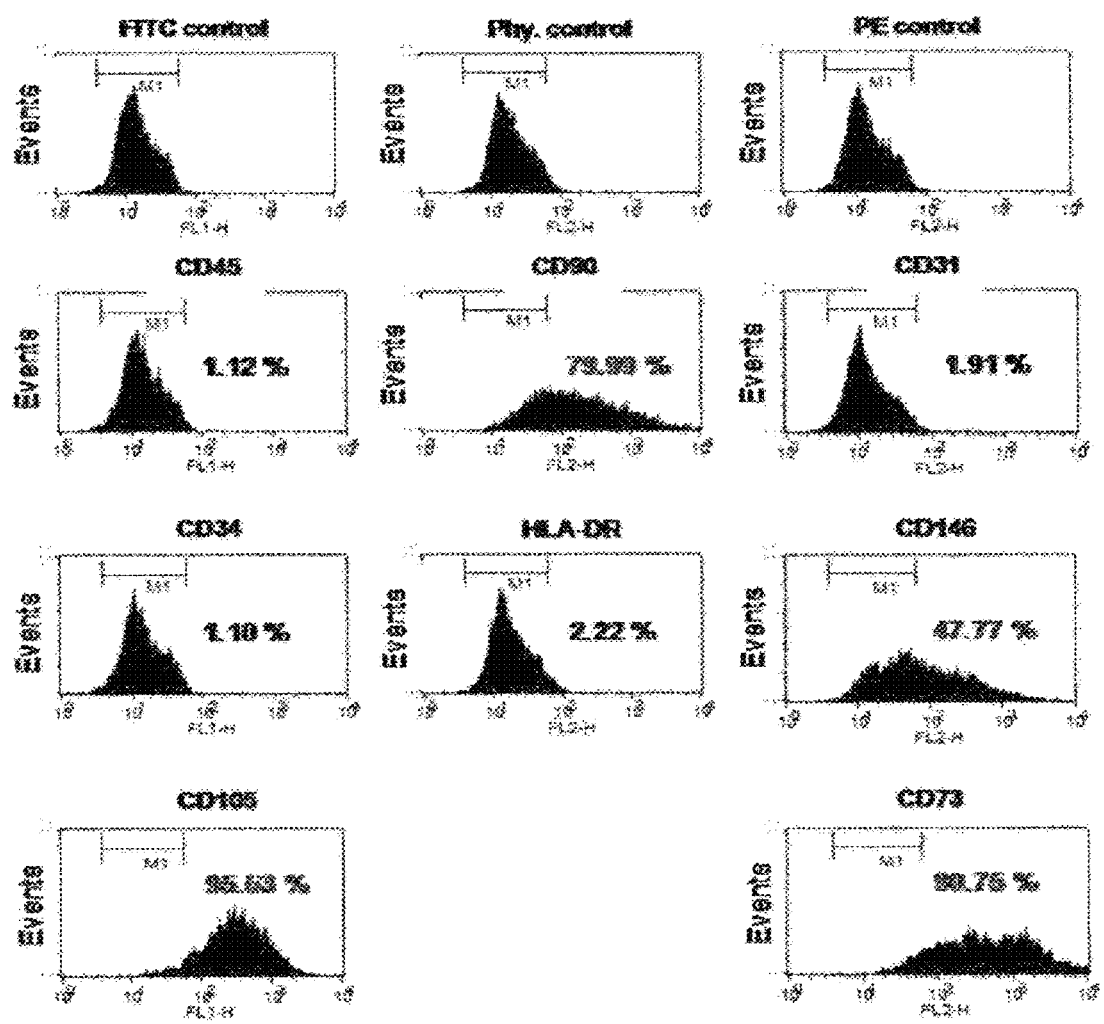
FIG. 1B shows markers which identify mesenchymal stem cells (MSCs) identified on the surface of hPMSCs.

FIG. 1B shows a surface pattern of hPMSCs. As shown in FIG. 1B, it was confirmed that the mesenchymal cell markers, CD90, CD146, CD105, and CD72, were positive as the result of FACS analysis.

Example 2

Confirmation of Hyaluronic Acid Synthesis Increase in TAO Patients

Tears obtained from normal people and TAO patients (total of 26 samples) were used to perform western blotting, and amounts of hyaluronic acid synthase (HAS) were measured. A total of 10 μg protein was loaded Anti-HAS1 and HAS2 were cultured at 4° C. ELISA analysis was also performed on the tears obtained from the TAO patients.

Figure 2:
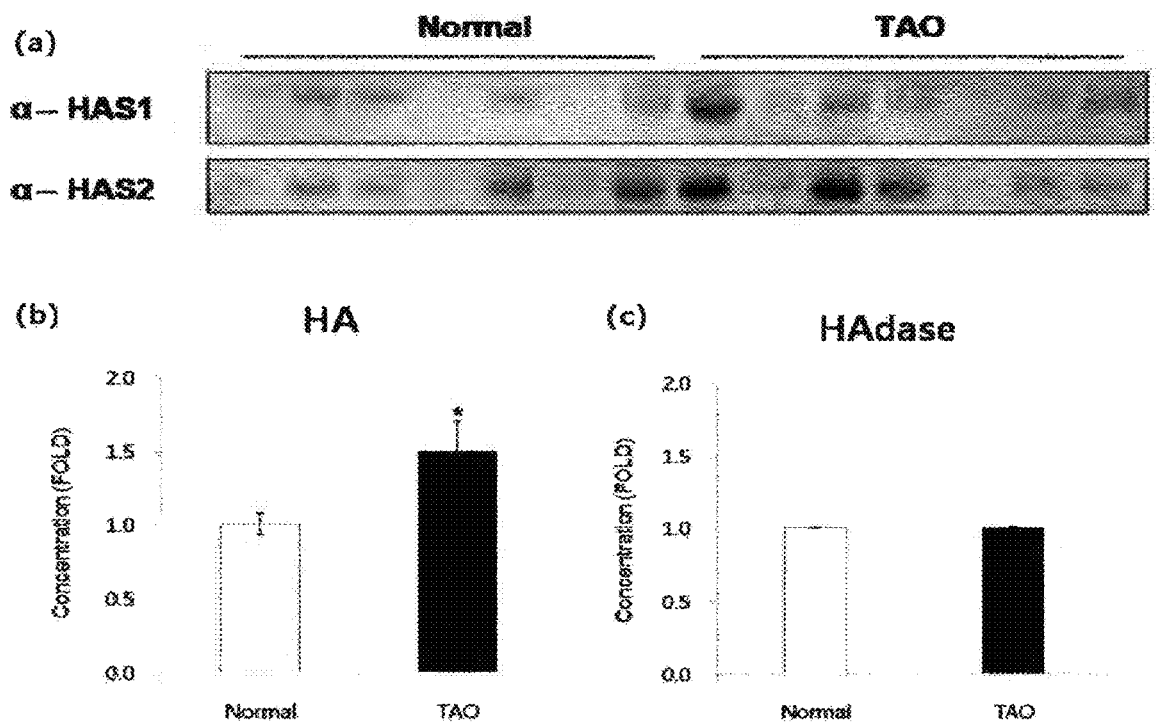
FIG. 2 shows the results of immunoassay confirming HAS, HA, and HAdase included in tears of a normal person and a patient with thyroid-associated ophthalmopathy (TAO)

As a result, it was confirmed that protein expressions of the hyaluronic acid synthases, HAS1 and HAS2, increased in the tears of the TAO patients compared to those of tears obtained from the normal people as shown in FIG. 2A. As shown in FIG. 2B, an increase of the level of Ha was also observed, but it was confirmed that the level of HAdase did not have a significant change as shown in FIG. 2C.

As a result of the ELISA analysis, the level of hyaluronic acid in the tears of the TAO patients increased, but the level of HAdase was not different from that of the normal people. Therefore, it was confirmed that production of hyaluronic acid increased as the HAdase increased in the TAO patients.
*77

Example 3

Confirmation of Hyaluronic Acid Production Decrease Effect of hPMSCs

On day 15 of culturing fibroblasts, the orbital fibroblasts were cultured together with IL-1β (20 ng/mL) as a stimulant during an adipose production inducing process. After co-culturing with hPMSCs, protein expression of HAS2 was determined.

Figure 3A:
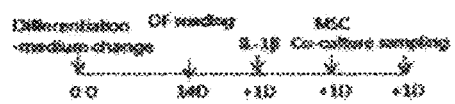
FIG. 3A shows co-culturing of orbital fibroblasts and hPMSCs and the results of measuring changes in HAS2 expression by western blotting.
Figure 3A:
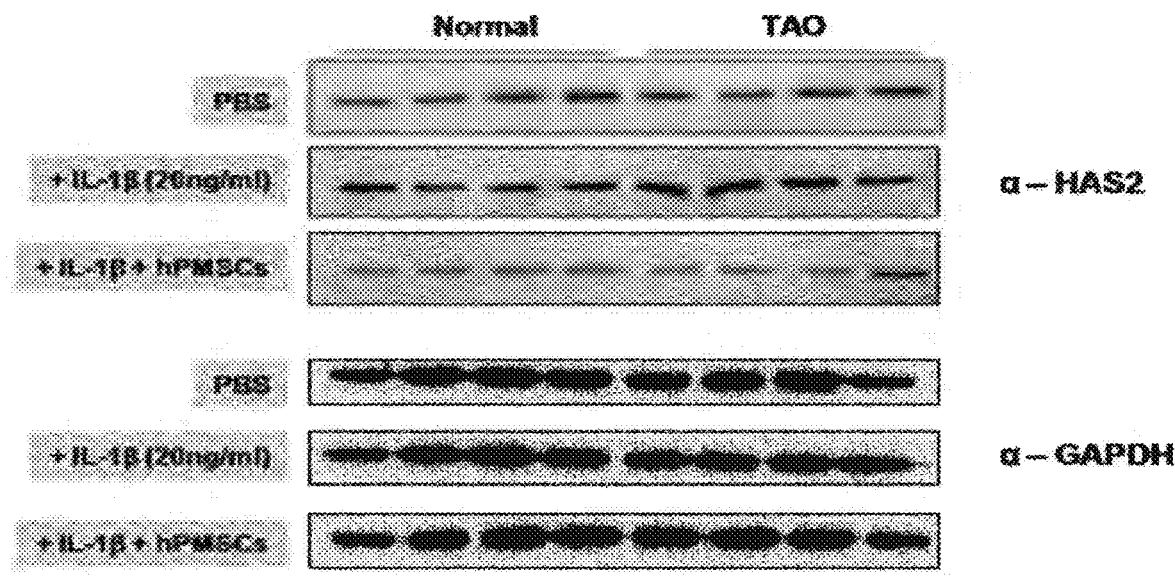

As shown in FIG. 3A, it was confirmed that expression of the hyaluronic acid sythase, HAS2, in the fibroblasts of the TAO patients increased, and that the protein expression of the synthase increased through the co-culture with PMSCs decreased.

Figure 3B:
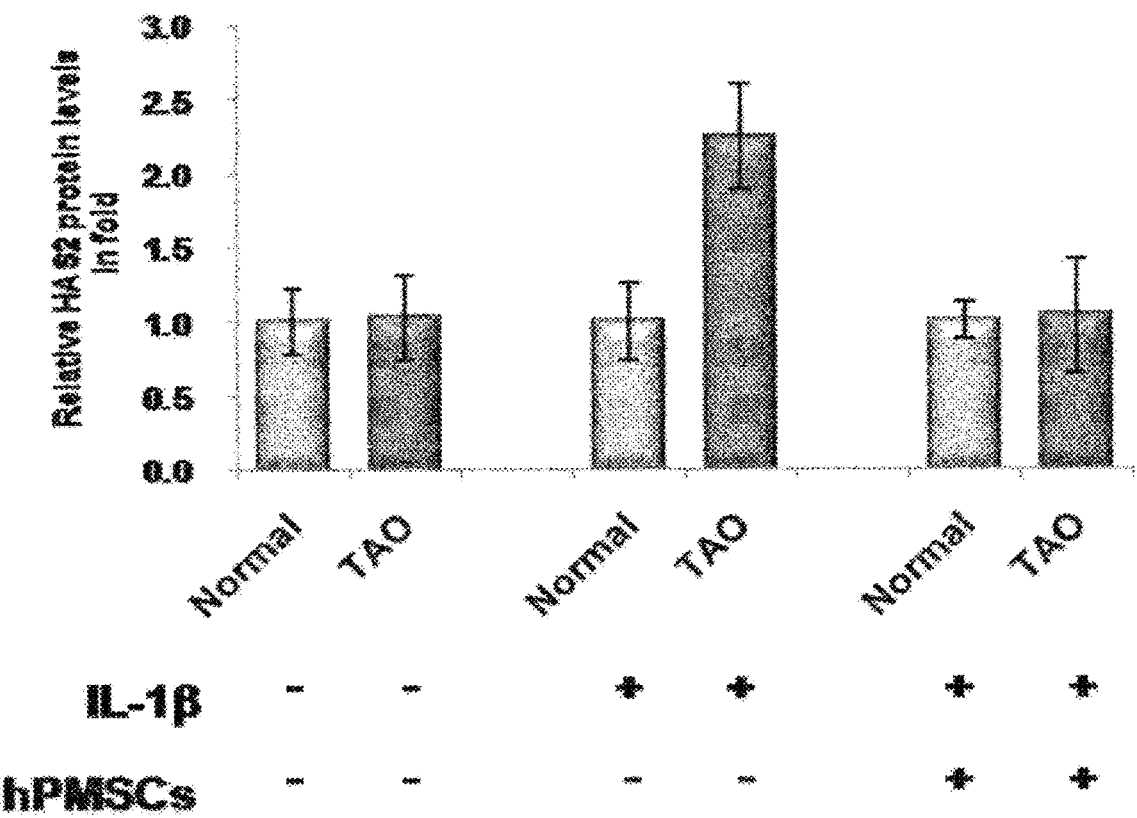
FIG. 3B shows co-culturing of orbital fibroblasts and hPMSCs and the quantified values of the changes in HAS2 expression.

Also, as shown in FIG. 3B, the protein expression level of the hyaluronic acid sythase, HAS2, was quantified, and the result showed that the fibroblasts of the TAO patients cultured in an adipose production inducing differentiation medium increased protein expression of HAS2 about 2.3 folds by the IL-1β stimulation, which was reduced by co-culture with PMSCs.

Example 4

Confirmation of Effects on Orbital Fibroblast Surface Antigen Markers of hPMSCs

The orbital fibroblasts obtained from the normal people and TAO patients were co-cultured with hPMSCs, and changes thus occurred were observed. The fibroblasts were analyzed by using FACS.

On day 15 of culturing the fibroblasts, the fibroblasts were treated with IL-1β (20 ng/mL). After 24 hours of culturing, hPMSCs were co-cultured with the resultant. The co-cultured fibroblasts were classified by CD90 or CD105 markers. Also, the fibroblasts were observed through a microscope.

Figure 4A:
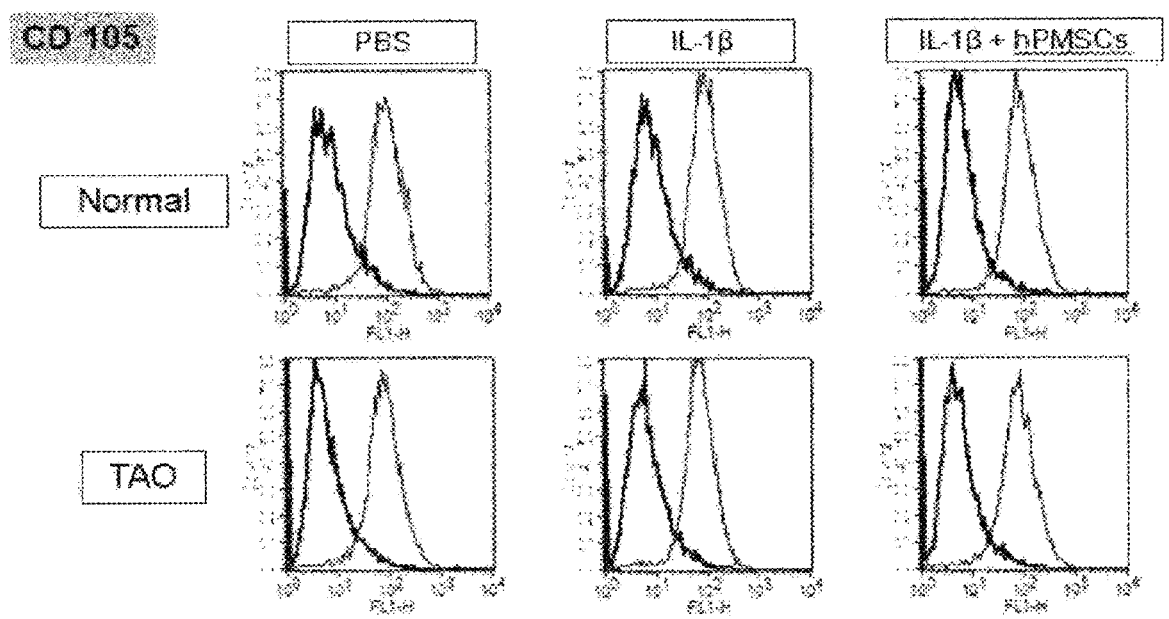
FIGS. 4A and 4B show the results of observing changes of surface markers of the co-cultured fibroblasts after co-culturing orbital fibroblasts with hPMSCs from a normal person and a TAO patient.
Figure 4B:
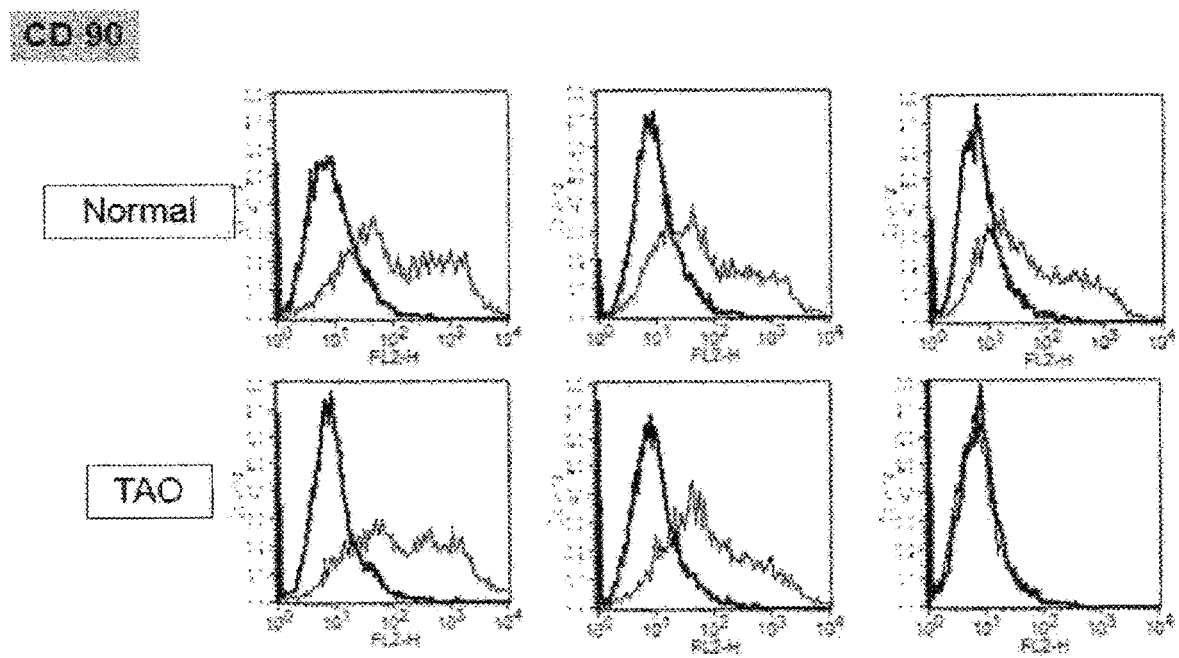

As shown in FIGS. 4A and 4B, it was confirmed that CD90 in the fibroblasts of the TAO patients changed by the co-culturing with hPMSCs as the result of analyzing changes of CD105 and CD90 which are fibroblasts of the normal people and patients.
*87

Example 5

Confirmation of Effect of hPMSCs on Adipogenesis

Orbital fibroblasts obtained from the normal people and TAO patients were cultured with adipose differentiation inducing medium 1 (33 μM biotin, 17 μM pantothenic acid, 0.2 nM T3, 10 μg/mL transferrin, 0.2 μM prostaglandin 12, 0.1 mM isobutylmethylxanthine (IBMX), 1 μM dexamethasone, and 5 μg/ml insulin) for 4 days, and the resultant was cultured with adipose differentiation inducing medium 2 (33 μM biotin, 17 μM pantothenic acid, 0.2 nM T3, 10 μg/mL transferrin, 0.2 μM prostaglandin 12, and 0.1 mM) from the 5th day to 10th day. On day 8 of the culturing, the orbital fibroblasts being cultured in the adipose differentiation medium were co-cultured with hPMSCs ($2\times10^5$) for 48 hours. Thereafter, mRNA expression of PPARγ, ADIPONECTIN, and C/EBPα, which are representative adipogenesis-related factors, were confirmed described in relation to Reference Example 5, and the results are shown in FIG. 5.

Figure 5:
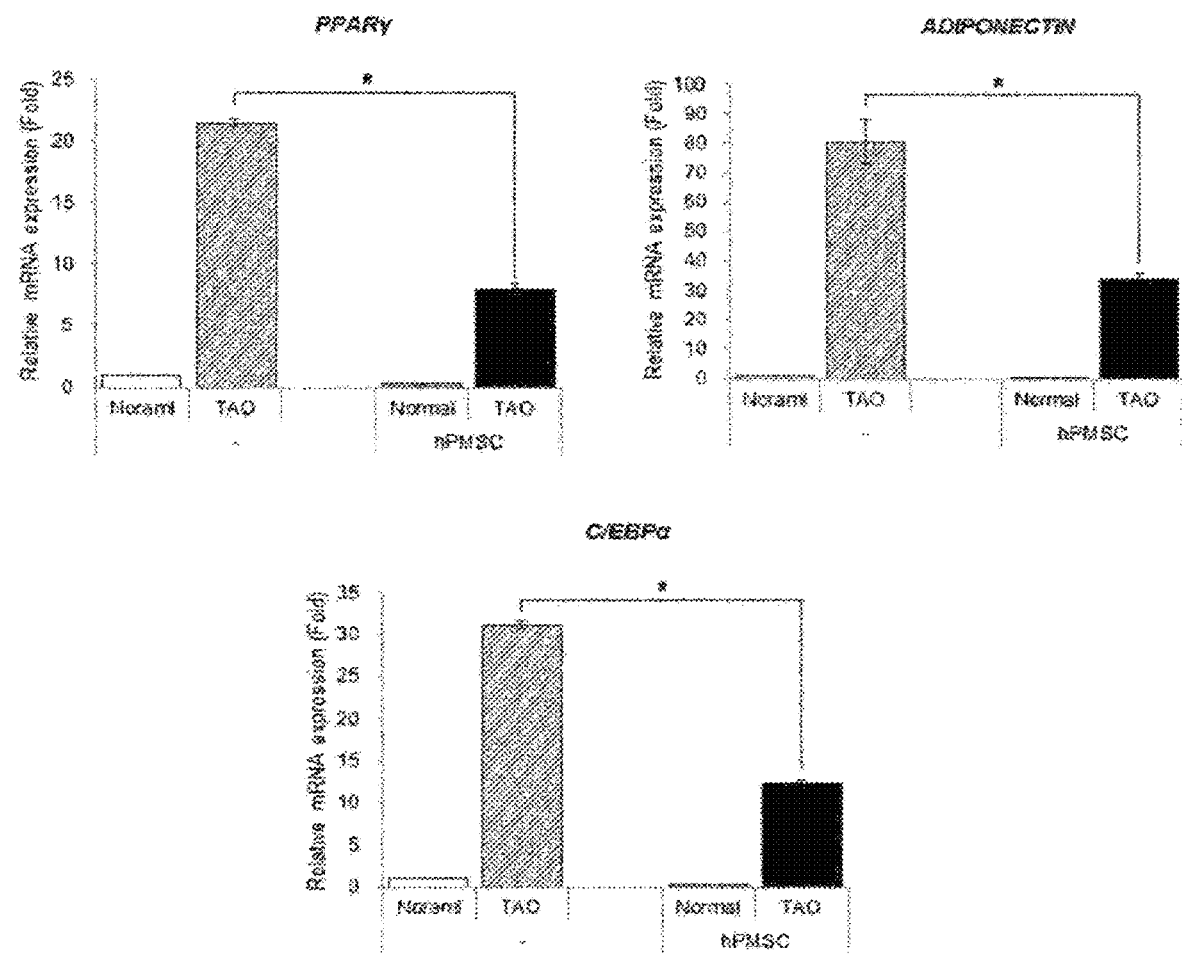
FIG. 5 shows the results of analyzing mRNA expression of PPARγ, ADIPONECTIN, and C/EBPα by using real-time PCR after co-culturing orbital fibroblasts with hPMSCs from a normal person and a TAO patient.

As a result, as shown in FIG. 5, it was confirmed that mRNA expression of PPARγ, ADIPONECTIN, and C/EBPα in the fibroblasts of the patients cultured in the adipose differentiation inducing medium increased 21.5 folds, about 80 folds, and 33 folds, each respectively. Whereas, it was confirmed that mRNA expression of PPARγ, mRNA expression of ADIPONECTIN, and mRNA expression of C/EBPα that all increased by the co-culturing with PMSCs decreased to about 8 folds, about 33 folds, and about 12.4 folds, each respectively. Therefore, the results shown above confirmed that the mesenchymal stem cells suppressed expressions of PPARγ, ADIPONECTIN, and C/EBPα of orbital fibroblasts, and this indicates that the mesenchymal stem cells suppress adipogenesis property of the orbital fibroblasts.

Example 6

Confirmation of Lipid Accumulation of Orbital Fibroblasts

Effects of human placenta-derived mesenchymal stem cells (PMSCs) on lipid accumulation of orbital fibroblasts were confirmed. In particular, the orbital fibroblasts obtained from the normal people and TAO patients were co-cultured with PMSCs as well as adipogenesis inducing medium culture. After 10 days, lipid accumulation in the orbital fibroblasts were confirmed as described in Reference Example 3 by using Oil-Red O staining, and the results are shown in FIG. 6.

Figure 6:
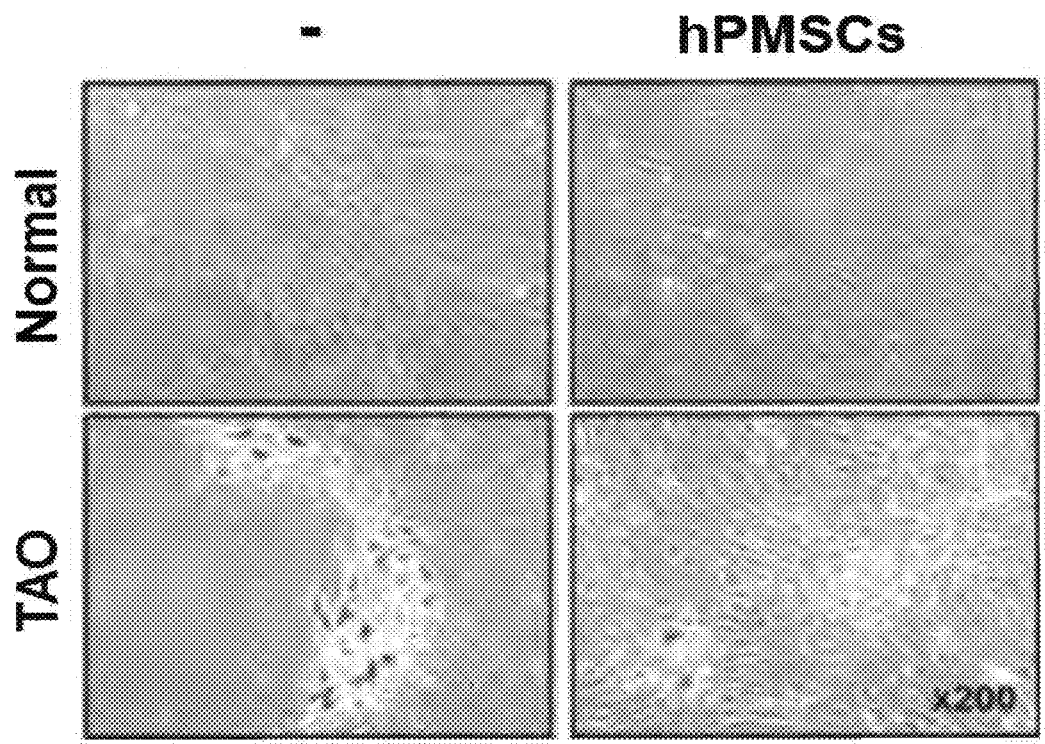
FIG. 6 shows the results of observing changes in lipid accumulation of fibroblasts after co-culturing orbital fibroblasts with hPMSCs from a normal person and a TAO patient.

As a result, it was confirmed that lipid accumulation of the fibroblasts of the TAO patients induced in the differentiation medium reduced by the co-culturing with PMSCs as shown in FIG. 6.

From these results, it was confirmed that the hPMSCs reduce abnormal activity of the fibroblasts of the TAP patients.

Example 7

Confirmation of Immunoregulatory Ability of Mesenchymal Stem Cells

In order to confirm immunoregulatory abilities of orbital fibroblasts of placenta-derived mesenchymal stem cells, adipose-derived mesenchymal stem cells, and bone marrow-derived mesenchymal stem cells isolated as described in Reference Example 1, the mesenchymal stem cell in naïve state were treated with inflammation inducing factors, and expression of the factors each expressed in the mesenchymal stem cells were compared with expression according to inflammatory reaction. The adipose-derived mesenchymal stem cells and bone marrow-derived mesenchymal stem cells were provided from the American Type Culture Collection (ATCC).

Particularly, the inflammation inducing factors, LPS and IL-1β, were each treated on the mesenchymal stem cells at 1 ng or 10 ng, respectively. Then, expression levels of immunoregulatory factors, hFOXP3, hHLA-G, and hTRL4, were confirmed by qRT-PCR. In particular, qRT-PCR was performed in steps including collecting cells treated with inflammation inducing factors and performing cell lysis using TRIZOL; synthesizing cDNA by using a reverse transcriptase; amplifying PCR by using a gene specific base sequence and a Tag. DNA polymerase; and performing electrophoresis on the amplified PCR product to on an agarose gel to confirm the presence of the amplified gene. The results of qRT-PCR analysis are shown in FIG. 7.

Figure 7A:
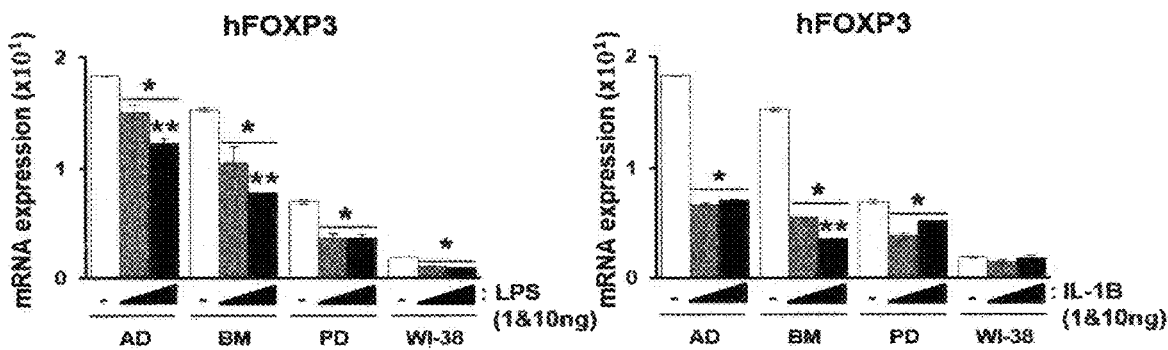
FIG. 7 is a graph showing the effect that mesenchymal stem cells according to an embodiment have on immune response regulatory factors of inflammation-induced cells; wherein AD: adipose-derived mesenchymal stem cells, BM: bone marrow-derived mesenchymal stem cells, PD: placenta-derived mesenchymal stem cells, WI-38: fibroblasts; a: FOXP3, b: HLA-G, c: hTRL4; *Control vs. Others: decrease, # Control vs. Others: increase, ** 1 ng vs. 10 ng: decrease, ##1 ng vs. 10 ng: increase.
Figure 7B:
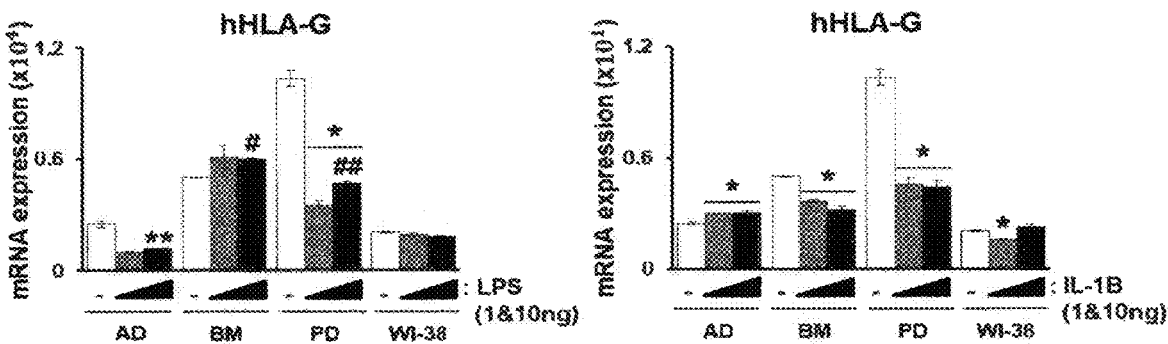
Figure 7C:
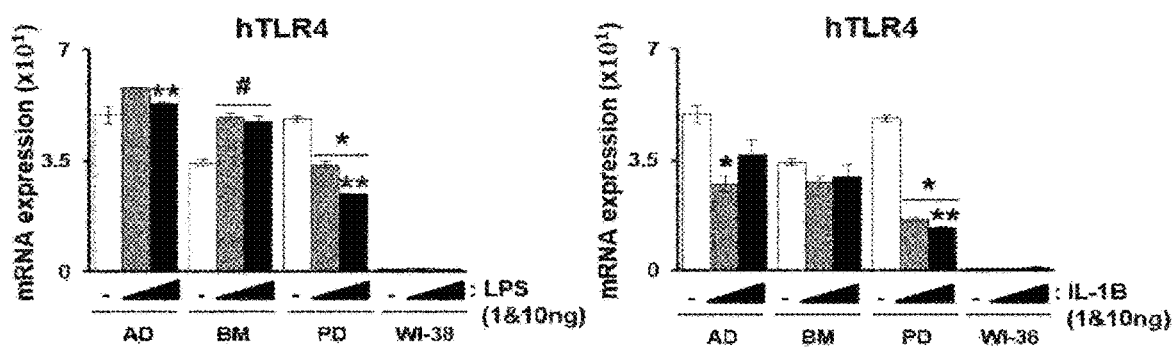

FIG. 7 is a graph that shows effects of the mesenchymal stem cells according to an embodiment on immune reaction regulatory factors of inflammation induced cells. AD: adipose-derived mesenchymal stem cell, BM: bone marrow-derived mesenchymal stem cell, PD: placenta-derived mesenchymal stem cell, WI-38: fibroblasts; a: FOXP3, b: HLA-G, c: hTRL4; *Control vs. Others: decrease, # Control vs. Others: increase, ** 1 ng vs. 10 ng: decrease, ## 1 ng vs. 10 ng: increase.

As shown in FIG. 7, it may be known that the mesenchymal stem cells according to an embodiment express HLA-G, FOXP3, and TLR4 more than the fibroblasts do. Particularly, the placenta-derived mesenchymal stem cells not only expressed FOXP3 and TLR4 as well as HLA-G known for protecting cells from T-cell attack by involved in immune response regulation than other cells and had high expression level after being treated with inflammation inducing factors. It may be known that mesenchymal stem cells (particularly, placenta-derived mesenchymal stem cells) exhibiting overexpression of an immuneregulatory ability factor, such as HLA-G, may be effectively used as a treating agent of thyroid-associated ophthalmopathy by analyzing change in expression as expression patterns of the immune-associated factors are treated with the inflammation inducing factors in a naive state.

The invention claimed is:

1. A method of treating or preventing thyroid-associated ophthalmopathy, the method comprising administering mesenchymal stem cells expressing at least one selected gene from the group consisting of forkhead box P3 (FOXP3), human leukocyte antigen G (HLA-G), and toll-like receptor 4 (TLR4), a cell population thereof, or a culture, a lysate, or an extract thereof, as an active ingredient, to a subject in need thereof.

2. The method of claim 1, wherein the stem cells have a characteristic a) or b) below:
   a) a characteristic of expressing at least one gene selected from the group consisting of chemokine (C-X-C motif) ligand 1 (CXCL-1), monocyte chemotactic protein 1 (MCP-1), and a tissue inhibitor of metalloproteinases (TIMP-1); or
   b) a surface antigen characteristic of at least one gene selected from the group consisting of CD90, CD146, CD105, and CD73.

3. The method of claim 1, wherein the mesenchymal stem cells are umbilical cord-derived, umbilical cord blood-derived, bone marrow-derived, placenta-derived, or adipose-derived mesenchymal stem cells.

4. The method of claim 1, wherein the mesenchymal stem cells are placenta chorion-derived mesenchymal stem cells.

5. The method of claim 1, wherein the mesenchymal stem cells suppress differentiation of orbital fibroblasts into adipocytes or production of hyaluronic acid.

6. The method of claim 1, wherein the thyroid-associated ophthalmopathy occurs in association with hyperthyroidism.

7. The method of claim 1, wherein the mesenchymal stem cells are for ocular administration.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: fprimer for PPAR

<400> SEQUENCE: 1
ttgacccaga aagcgattc                                                    19

<210> SEQ ID NO 2
<211> LENGTH: 20
<212> TYPE: DNA
<213> ORGANISM: Artificial Sequence
<220> FEATURE:
<223> OTHER INFORMATION: Reverse primer for PPAR

<400> SEQUENCE: 2
aaagttggtg ggccagaatg                                                   20

<210> SEQ ID NO 3
<211> LENGTH: 21
<212> TYPE: DNA
<213> ORGANISM: Artificial Sequence
<220> FEATURE:
<223> OTHER INFORMATION: Forward primer for ADIPONECTIN

<400> SEQUENCE: 3
ggccgtgatg atggcagaga t                                                 21

<210> SEQ ID NO 4
<211> LENGTH: 22
<212> TYPE: DNA
<213> ORGANISM: Artificial Sequence
<220> FEATURE:
<223> OTHER INFORMATION: Reverse primer for ADIPONECTIN

<400> SEQUENCE: 4
tttcaccgat gtctccctta gg                                                22

<210> SEQ ID NO 5
```

-continued

```
<211> LENGTH: 20
<212> TYPE: DNA
<213> ORGANISM: Artificial Sequence
<220> FEATURE:
<223> OTHER INFORMATION: Forward primer for C/EBP

<400> SEQUENCE: 5 tgtataccec tggtgggaga                                               20

<210> SEQ ID NO 6
<211> LENGTH: 20
<212> TYPE: DNA
<213> ORGANISM: Artificial Sequence
<220> FEATURE:
<223> OTHER INFORMATION: reverse primer for C/EBP

<400> SEQUENCE: 6
tcataactcc ggtccctctg                                               20
```